US010867134B2

United States Patent
Kimura

(10) Patent No.: US 10,867,134 B2
(45) Date of Patent: Dec. 15, 2020

(54) METHOD FOR GENERATING TEXT STRING DICTIONARY, METHOD FOR SEARCHING TEXT STRING DICTIONARY, AND SYSTEM FOR PROCESSING TEXT STRING DICTIONARY

(71) Applicant: HITACHI HIGH-TECHNOLOGIES CORPORATION, Tokyo (JP)

(72) Inventor: Kouichi Kimura, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 148 days.

(21) Appl. No.: 16/325,737

(22) PCT Filed: Sep. 2, 2016

(86) PCT No.: PCT/JP2016/075747
§ 371 (c)(1),
(2) Date: Feb. 15, 2019

(87) PCT Pub. No.: WO2018/042609
PCT Pub. Date: Mar. 8, 2018

(65) Prior Publication Data
US 2019/0205394 A1 Jul. 4, 2019

(51) Int. Cl.
*G06F 40/30* (2020.01)
*G06F 16/00* (2019.01)
(Continued)

(52) U.S. Cl.
CPC .............. *G06F 40/30* (2020.01); *G06F 16/00* (2019.01); *G06F 40/242* (2020.01); *G16B 30/00* (2019.02);
(Continued)

(58) Field of Classification Search
CPC .. G06F 17/30445; G06F 17/2785; G06F 7/36; G06F 19/3437
See application file for complete search history.

(56) References Cited

U.S. PATENT DOCUMENTS 6,363,174 B1 *  3/2002  Lu ............................ G06F 16/35
                                              382/209
6,466,902 B1 * 10/2002  Lu ........................... G06F 40/242
                                              704/9

(Continued)

OTHER PUBLICATIONS

Paolo Ferragina, et al., "Opportunistic Data Structures with Applications", Proceedings of the 41st Symposium on Foundations of Computer Science (FOCS 2000), Los Alamitos, CA, USA: IEEE Computer Society; 2000, pp. 390-398.

(Continued)

*Primary Examiner* — Anne L Thomas-Homescu
(74) *Attorney, Agent, or Firm* — Mattingly & Malur, PC

(57) ABSTRACT

A multicore CPU of a text string data analyzing device: loads a plurality of blocks obtained by dividing a text string dictionary into a memory; executes, in parallel on block groups executable independently of each other, an entry registration process of registering, character by character, unregistered text strings of text string data as new entries in the blocks in order from last characters; and outputs, as BW transformed data of the text string dictionary in which the text string data is already registered, a text string obtained by coupling text strings registered in entries of the blocks in a state in which no unregistered text strings of the blocks exists.

6 Claims, 12 Drawing Sheets

(51) Int. Cl.
  *H03M 7/30* (2006.01)
  *G16B 30/00* (2019.01)
  *G06F 40/242* (2020.01)
(52) U.S. Cl.
  CPC ....... *H03M 7/3068* (2013.01); *H03M 7/3088* (2013.01)

(56) References Cited

U.S. PATENT DOCUMENTS

| | | | | |
|---|---|---|---|---|
| 8,533,166 | B1* | 9/2013 | Sulieman | G06F 16/183 707/693 |
| 8,798,936 | B2* | 8/2014 | Bauer | G16B 50/50 702/19 |
| 8,990,217 | B2* | 3/2015 | Jagmohan | H03M 7/3084 707/741 |
| 9,137,336 | B1* | 9/2015 | Zalunin | H03M 7/30 |
| 9,547,588 | B1* | 1/2017 | Biederman | G06F 12/0246 |
| 10,025,774 | B2* | 7/2018 | Coulet | G06F 40/30 |
| 10,437,825 | B2* | 10/2019 | Goodwin | G06F 16/258 |
| 10,622,094 | B2* | 4/2020 | Kim | C12Q 1/6816 |
| 10,678,613 | B2* | 6/2020 | Frech | G06F 9/451 |
| 2004/0139118 | A1* | 7/2004 | Yach | H03M 7/30 |
| 2007/0255748 | A1* | 11/2007 | Ferragina | G06F 16/9027 |
| 2008/0126378 | A1* | 5/2008 | Parkinson | H04L 9/3268 |
| 2008/0152235 | A1* | 6/2008 | Bashyam | H04N 19/99 382/224 |
| 2009/0063465 | A1* | 3/2009 | Ferragina | G06F 16/316 |
| 2009/0210437 | A1* | 8/2009 | Kuila | H03M 7/6041 |
| 2010/0281079 | A1* | 11/2010 | Marwah | H03M 7/30 707/812 |
| 2011/0153623 | A1* | 6/2011 | Vo | G06F 16/284 707/752 |
| 2012/0109908 | A1* | 5/2012 | Barsness | G06F 16/21 707/693 |
| 2012/0124016 | A1* | 5/2012 | Barsness | G06F 16/1744 707/693 |
| 2012/0254333 | A1* | 10/2012 | Chandramouli | G06Q 10/107 709/206 |
| 2013/0013574 | A1* | 1/2013 | Wu | H03M 7/3077 707/693 |
| 2013/0051690 | A1* | 2/2013 | Kuettel | G06F 16/13 382/232 |
| 2013/0138428 | A1* | 5/2013 | Chandramouli | G06F 40/40 704/9 |
| 2014/0129830 | A1* | 5/2014 | Raudaschl | G06F 21/6272 713/165 |
| 2015/0006475 | A1* | 1/2015 | Guo | G06F 16/1752 707/609 |
| 2015/0178305 | A1* | 6/2015 | Mueller | G06F 16/221 707/693 |
| 2015/0235143 | A1* | 8/2015 | Eder | G16H 50/50 706/12 |
| 2015/0317449 | A1* | 11/2015 | Eder | A61M 5/1723 600/595 |
| 2015/0331907 | A1* | 11/2015 | Bruestle | G06F 16/951 707/696 |
| 2015/0347088 | A1* | 12/2015 | Bruestle | G16B 30/00 707/753 |
| 2018/0011869 | A1* | 1/2018 | Senthil | H03M 7/3084 |
| 2019/0006048 | A1* | 1/2019 | Gupta | G16H 20/10 |

OTHER PUBLICATIONS

Ross A. Lippert, et al., "A Space-Efficient Construction of the Burrows-Wheeler Transform for Genomic Data", Journal of Computational Biology, 2005, vol. 12, No. 7, pp. 943-951.
Paolo Ferragina, et al., "Lightweight Data Indexing and Compression in External Memory", Latin 2010: Theoretical Informatics, vol. 6034 of the series Lecture Notes in Computer Science, Springer, pp. 697-710.
Heng Li, "Fast construction of FM-index for long sequence reads", Bioinformatics Advance Access, Aug. 8, 2014, pp. 1-2.
International Search Report of PCT/JP2016/075747 dated Nov. 29, 2016.

* cited by examiner

METHOD FOR GENERATING TEXT STRING DICTIONARY, METHOD FOR SEARCHING TEXT STRING DICTIONARY, AND SYSTEM FOR PROCESSING TEXT STRING DICTIONARY

TECHNICAL FIELD

The present invention relates to a method for generating a text string dictionary, a method for searching a text string dictionary, and a system for processing a text string dictionary.

BACKGROUND ART

Due to the progress of deoxyribonucleic acid (DNA) sequencing technologies, amounts of DNA sequence data output by DNA sequencers have been rapidly increasing. Thus, calculation costs required for data analysis such as mutational analysis for checking whether or not DNA sequence data with a large amount contains a deleterious mutant sequence have also been increasing.

To improve the efficiency of the data analysis, it is effective to sort, in alphabetical order (lexicographic order), DNA sequence data (text string data) output in the order that the DNA sequence data is measured. This is due to the fact that the sorted data can be searched at a high speed. Especially, as a method suitable for the DNA sequence data, a method using Burrows-Wheeler (BW) transform (or FM index) is known (Nonpatent Literature 1).

DNA sequence data subjected to BW transform is expressed as a single string including a DNA and a delimiter ($) as elements. Each of the elements corresponds to a respective one of elements of a list in which all suffixes of all sequences included in the original DNA sequence data are sorted in alphabetical order. In addition, an efficient method for using results of BW transform as a dictionary obtained by sorting all suffixes in alphabetical order is known (Nonpatent Literature 1). Results of BW transform are also referred to as a text string dictionary.

Since the size of DNA sequence data is large, generation of a text string dictionary requires a significant calculation cost. A method for generating a text string dictionary at a high speed is known (Patent Literature 1, Nonpatent Literature 2, and Nonpatent Literature 3). To further increase the speed, a method for parallelizing the generation of the text string dictionary for each of base types (alphabetical characters) A, C, G, and T is known (Nonpatent Literature 4). As a result, a parallelization degree that is nearly equal to the number (alphabet size) of the base types can be obtained and the speed becomes approximately 4 times higher, but a larger parallelization degree has not yet been obtained.

CITATION LIST

Patent Literature

Patent Literature 1: U.S. Pat. No. 8,798,936

Nonpatent Literature

Nonpatent Literature 1: Ferragina P, Manzini G. Proceedings of the 41st Symposium on Foundations of Computer Science (FOCS 2000). Los Alamitos, Calif., USA: IEEE Computer Society; 2000. Opportunistic data structures with applications; p. 390-398.

Nonpatent Literature 2: Lippert, Ross A., Clark M. Mobarry, and Brian P. Walenz. "A space-efficient construction of the Burrows-Wheeler transform for genomic data." Journal of Computational Biology 12.7 (2005): 943-951.

Nonpatent Literature 3: Ferragina P, Gagie T, Manzini G. "Lightweight Data Indexing and Compression in External Memory." LATIN 2010: Theoretical Informatics. Volume 6034 of the series Lecture Notes in Computer Science, Springer, pp 697-710.

Nonpatent Literature 4: Li, Heng. "Fast construction of FM-index for long sequence reads." Bioinformatics (2014): btu541.

SUMMARY OF INVENTION

Technical Problem

On the other hand, in a recent calculator, a multithread process using a CPU having a plurality of cores enables a text string dictionary to be generated at a speed higher by several tens of times with a parallelization degree larger by several tens of times in many cases. However, in a method for parallelizing the generation of a text string dictionary for a large amount of text string data for each of character types (Nonpatent Literature 4), a parallelization degree is suppressed to approximately an alphabet size (for example, approximately four times since the number of base types is 4 in the case of DNA sequence data). Thus, a calculator having several tens of CPU cores cannot effectively use all the cores to execute parallel calculation to increase the speed.

Thus, a method for parallel calculation that further improves a parallelization degree is considered. In general, to increase the speed of a process, the entire process is divided into partial processes, and the partial processes are executed in parallel in many cases. In the cases, since calculation results obtained in each of the partial processes are referenced in the other of the partial processes, and a shared memory, an input device, an output device, and the like are accessed in the partial processes, waiting (synchronization) is required in many cases. When such waiting frequently occurs, the waiting causes a reduction in processor utilization and prevents an increase in the speed of the process.

In addition, in general, calculation time periods required for the partial processes vary. When the number of partial processes is equal to or nearly equal to the number of CPU cores, calculation loads of the CPU cores are not balanced and it is difficult to effectively use all the CPU cores. To equalize calculation loads to be distributed to all the CPU cores and efficiently increase the speed of the process, it is necessary to divide the process into a sufficiently larger number of partial processes than the number of CPU cores. When this is executed, calculation loads of the cores can be equalized by dynamic load distribution by multithreading, and the speed of the process can be increased by efficient parallelization in which all the cores are effectively used.

A main object of the present invention is to provide a method for executing parallelization effectively using the number of CPU cores to increase the speed of a process of generating a text string dictionary in which text string data is registered.

Solution to Problems

To solve the aforementioned problems, a method for generating a text string dictionary of the present invention is to execute the following processes.

That is, in the present invention, the method is executed by a text string data analyzing device including a multicore CPU having a plurality of CPU cores and a memory.

The text string dictionary loaded in the memory is divided into a plurality of blocks, the blocks are added thereto respective labels different from each other, and the label includes an alphabet constituting text string data and one or more delimiters.

The method for generating a text string dictionary includes the steps, performed by the multicore CPU, of: registering, for each of the inputted text string data, the last character of the received text string data as an entry of the block in the blocks added thereto the labels of the delimiters, and making the last character associate with a remaining text string obtained by excluding the last character from the text string data, as an unregistered text string; executing an entry registration process in parallel on each of the blocks grouped into appropriate blocks executable independently of each other, the entry registration process comprising the substep of reading registration source blocks in which the unregistered text strings are associated with the entries of the blocks, the substep of registering last characters of the unregistered text strings of the registration source blocks as new entries in registration destination blocks identified from the labels and entries of the registration source blocks, and the substep of associating remaining text strings obtained by excluding the new entries from the unregistered text strings as new unregistered text strings; and outputting, as Burrows-Wheeler (BW) transformed data of the text string dictionary in which the text string data is already registered, a text string obtained by coupling text strings registered in the entries of the blocks in the order of alphabets indicated by the labels of the blocks and the delimiters in a state in which no unregistered text strings of the blocks exists.

Other means for solving the problems will be described hereinafter.

Advantageous Effects of Invention

In the present invention, it is possible to provide a method for executing parallelization effectively using the number of CPU cores to increase the speed of a process of generating a text string process in which text string data is registered.

DESCRIPTION OF EMBODIMENTS

Hereinafter, an embodiment of the present invention is described in detail with reference to the accompanying drawings.

Figure 1:
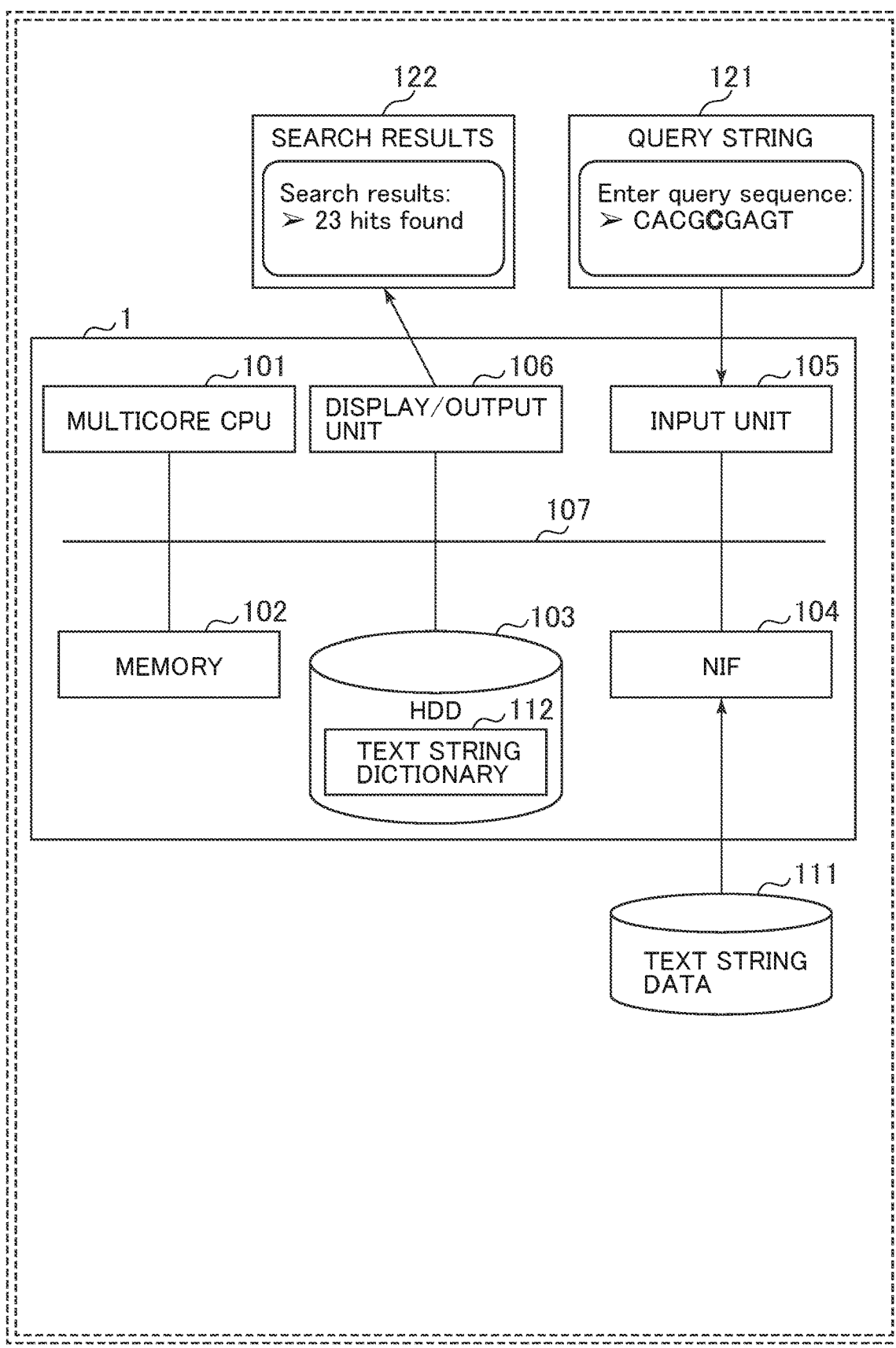
FIG. 1 is a configuration diagram showing a text string search system according to an embodiment of the present invention.

FIG. 1 is a configuration diagram showing a text string search system. A text string data analyzing device 1 is enabled by a computer such as a server having a configuration of a commonly-used calculator.

The text string data analyzing device 1 has a configuration in which a multicore central processing unit (CPU) 101, a memory 102, an HDD 103, an NIF 104, an input unit 105, and a display/output unit 106 are connected to a bus 107.

The multicore CPU 101 is a central processing unit having multiple cores and capable of executing parallel calculation. Various processes described later are executed by causing the multicore CPU 101 to execute a program.

The memory 102 is a storage unit configured to temporarily store the program and various types of work data.

The HDD 103 is a hard disk drive functioning as a storage unit configured to store a text string dictionary 112 and various types of work data. The text string dictionary 112 stored in the HDD 103 may be stored in a storage device externally connected to the text string data analyzing device 1 or may be stored in a data center connected via a network.

The NIF 104 is a network interface to be connected to the Internet or the like. The text string data analyzing device 1 is connected to an external device via a local area network (LAN) connected to the NIF 104, the Internet, or the like and accesses text string data 111 included in the connection destination. The text string data 111 is data to be registered in the text string dictionary 112.

The input unit 105 is input means such as a keyboard for inputting a command, a parameter, and the like. The input unit 105 receives an input query string (query sequence) 121.

The display/output unit 106 displays a graphical user interface (GUI) for an operation and an analysis result. The display/output unit 106 displays the number of appearances (hits) of the query string 121 or the like as results 122 of searching from the text string dictionary 112 using the query string 121 as a search key. Instead of the number of appearances, information indicating whether the query string 121 has appeared once or more (appearance) or has not appeared (no appearance) may be used.

Figure 2:
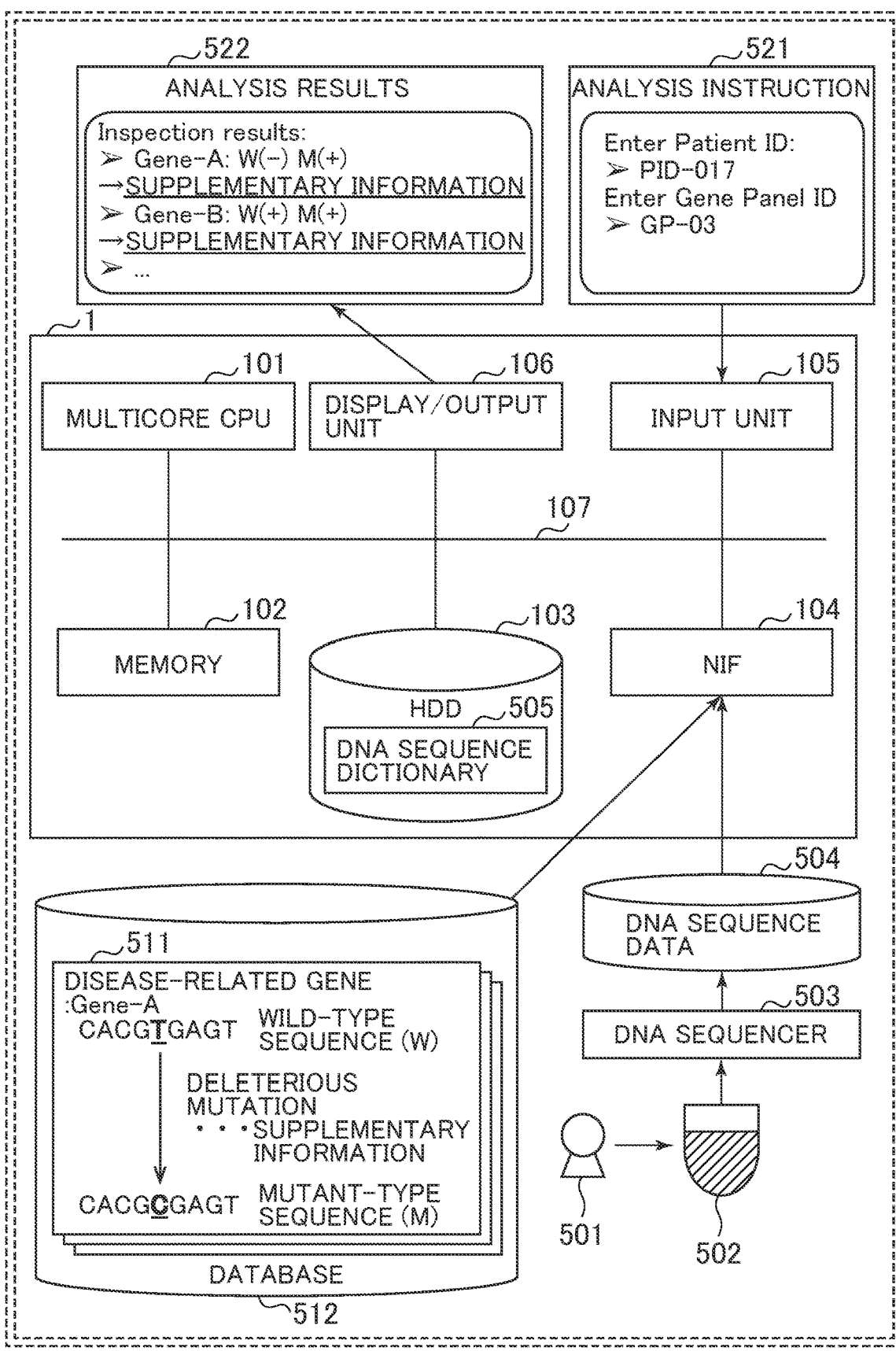
FIG. 2 is a diagram showing an example in which the text string search system shown in FIG. 1 is applied to a DNA analysis system according to the embodiment of the present invention.

FIG. 2 shows an example in which the text string search system shown in FIG. 1 is applied to a DNA analysis system. When DNA sequence data is used as the text string data 111, the text string search system is applicable to a DNA sequence data search system. When amino-acid sequence (protein) data is used as the text string data 111, the text string search system is applicable to a protein data search system.

DNA sequence data 504 that is results of causing a DNA sequencer 503 to analyze DNA samples 502 collected from patients 501 is used as the text string data 111 shown in FIG. 1.

The text string dictionary 112 is DNA sequence dictionaries 505 independent for the patients 501 and is generated based on the text string data 111.

First, the input unit 105 receives an analysis instruction 521 indicating a patient to be subjected to mutational analysis and a genetic panel to be used for the mutational analysis. The text string data analyzing device 1 acquires information of the indicated genetic panel 511 from a database 512 connected to the network via the NIF 104. The information of the genetic panel 511 includes a wild-type sequence W of each gene, a mutant-type sequence M. of each gene, and supplementary information (disease states caused by mutation, effective treatments, effective medical agents, and the like) on the mutation.

Next, the text string data analyzing device 1 treats a wild-type sequence and a mutant-type sequence as a query string 121 for each gene within the genetic panel 511 and checks whether or not each sequence of the query string 121 is already registered in the DNA sequence dictionary 505, thereby determining whether or not the query string 121 is detected in the DNA sample 502 of the patient 501. The display/output unit 106 displays or outputs the results of this determination as analysis results 522.

In addition, the display/output unit 106 uses a graphic user interface (GUI) or the like to provide a link to the supplementary information included in the genetic panel 511 for mutation detected from the analysis results 522. By tracing the link, reference information to be used to estimate the progress of a disease of the patient 501 and reference information to be used to select a treatment and a medical agent suitable for the patient 501 are obtained.

Figure 3:
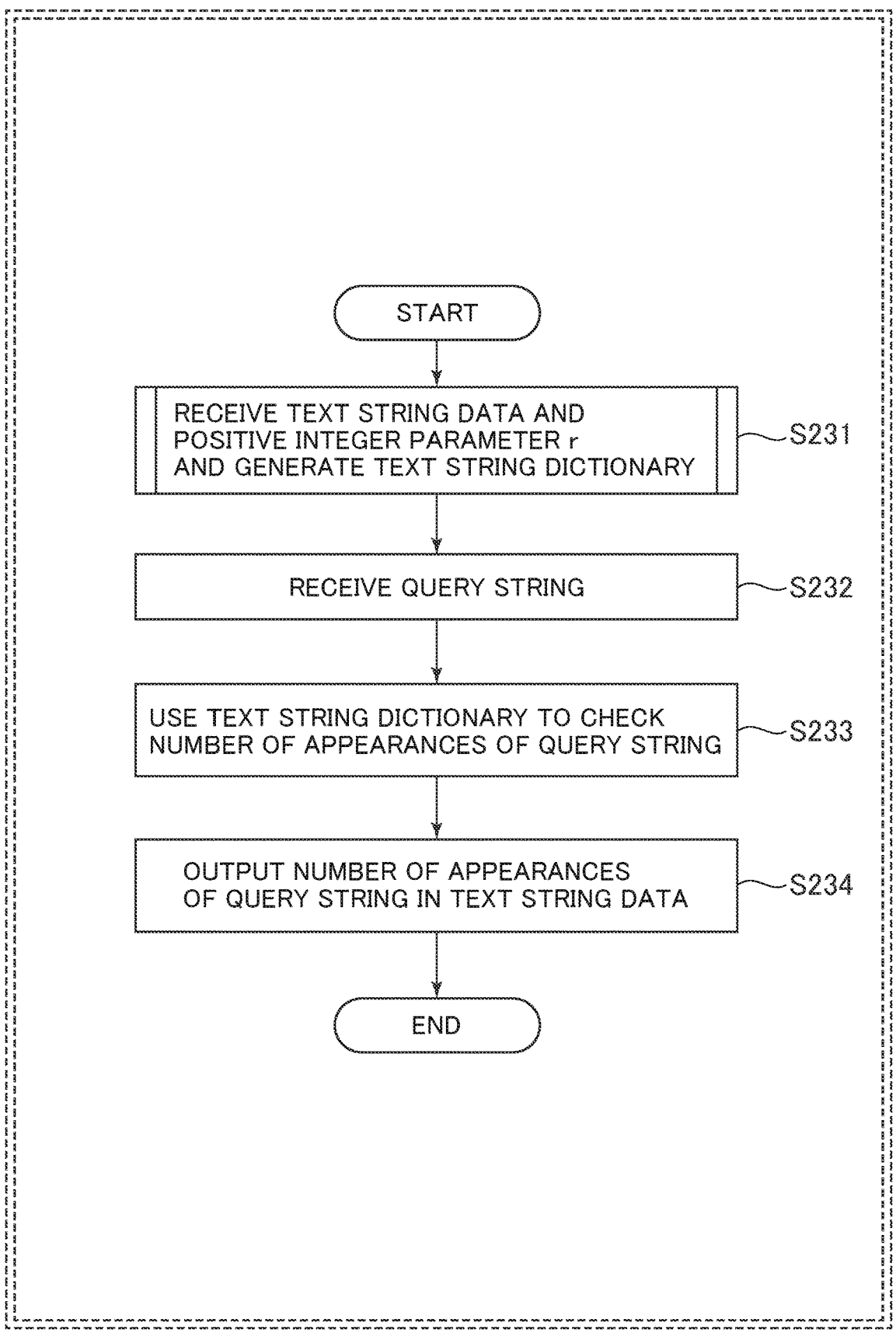
FIG. 3 is a flowchart showing an entire process of the text string search system shown in FIG. 1 according to the embodiment of the present invention.

FIG. 3 is a flowchart showing an entire process of the text string search system shown in FIG. 1.

In S231, the multicore CPU 101 receives the text string data 111 and a positive integer parameter r and generates the text string dictionary 112 (described in detail with reference to FIG. 4).

In S232, the multicore CPU 101 receives a query string 121.

In S233, the multicore CPU 101 uses a known high-speed search method (Nonpatent Literature 1) utilizing the text string dictionary 112 to check the number of appearances of the query string 121 in the text string data 111.

In S234, the multicore CPU 101 outputs or displays the number of appearances checked in S233 as search results 122.

Hereinafter, a data structure to be used in a process (S231) of generating the text string dictionary 112 is defined.

"Blocks" are obtained by dividing the text string dictionary 112 being generated and are configured as lists including alphabetical characters or delimiters as constituent elements (entries). An "empty block" is an empty list. The blocks are placed in a shared memory.

"Labels" are identifiers of the blocks and are used to identify the blocks serving as sources from which unregistered text strings are registered and destinations in which unregistered text strings are registered. Each of the labels is expressed by adding a delimiter symbol $ to the end of an alphabetical string having a length of r (r is a positive integer parameter) or to the end of an alphabetical string having a length of 0 or more and r−1 or less. A group of suffixes starting with a label w is referred to as "w block".

A "link" connects an entry within a block to a text string outside the block. A link connects a single entry (a link source) to a single link destination text string. In a block, an entry with or without a link may exist. Since the link destination text string is newly registered in an entry within a block, the link destination text string may be referred to as "unregistered text string" to be registered in the block at current time.

A single label is added to a single block. For example, a $ block 412 shown in FIG. 8 has a label "$". Blocks are indicated by rectangles, labels are indicated on the left side of the blocks, and link destination text strings are indicated on the right side of the blocks. For example, an "AATT" (link destination text string 413) is linked from a first entry "A" of the $ block 412.

Figure 4:
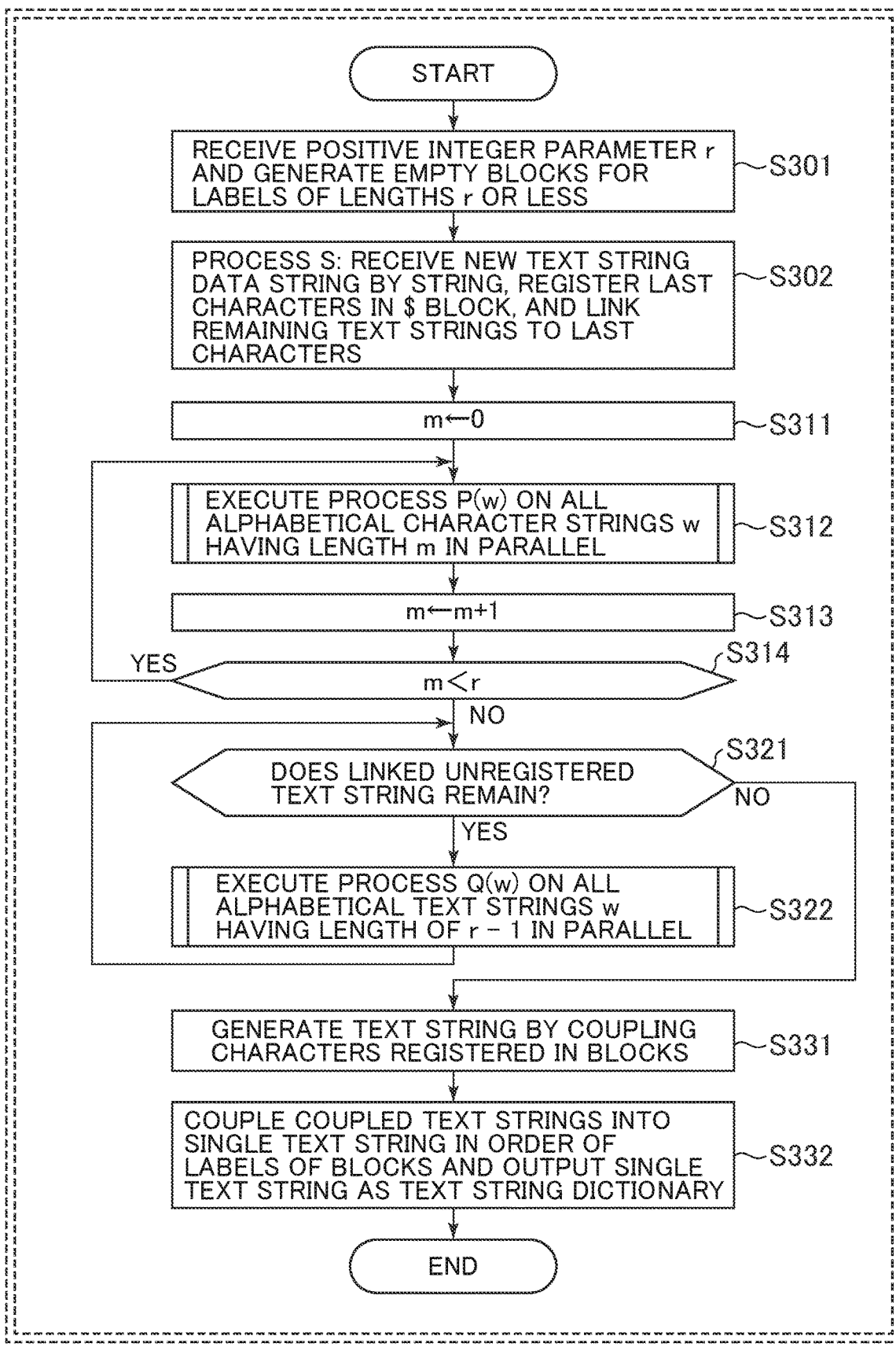
FIG. 4 is a flowchart showing details of a process of generating a text string dictionary according to the embodiment of the present invention.

FIG. 4 is a flowchart showing details of the process (S231) of generating the text string dictionary 112.

In S301, the multicore CPU 101 receives the positive integer parameter r and generates empty blocks for labels having lengths of r or less in the memory 102.

In S302, the multicore CPU 101 receives new text string data 111 via the NIF 104 string by string, registers the last characters of the received text strings in the $ block, and links the remaining text strings obtained by excluding the last characters from the received text strings to the last characters. The last characters of the received text strings may be referred to as suffixes (empty text strings E) with a length of 0.

In S311, the multicore CPU 101 sets a parameter m to 0.

Figure 5:
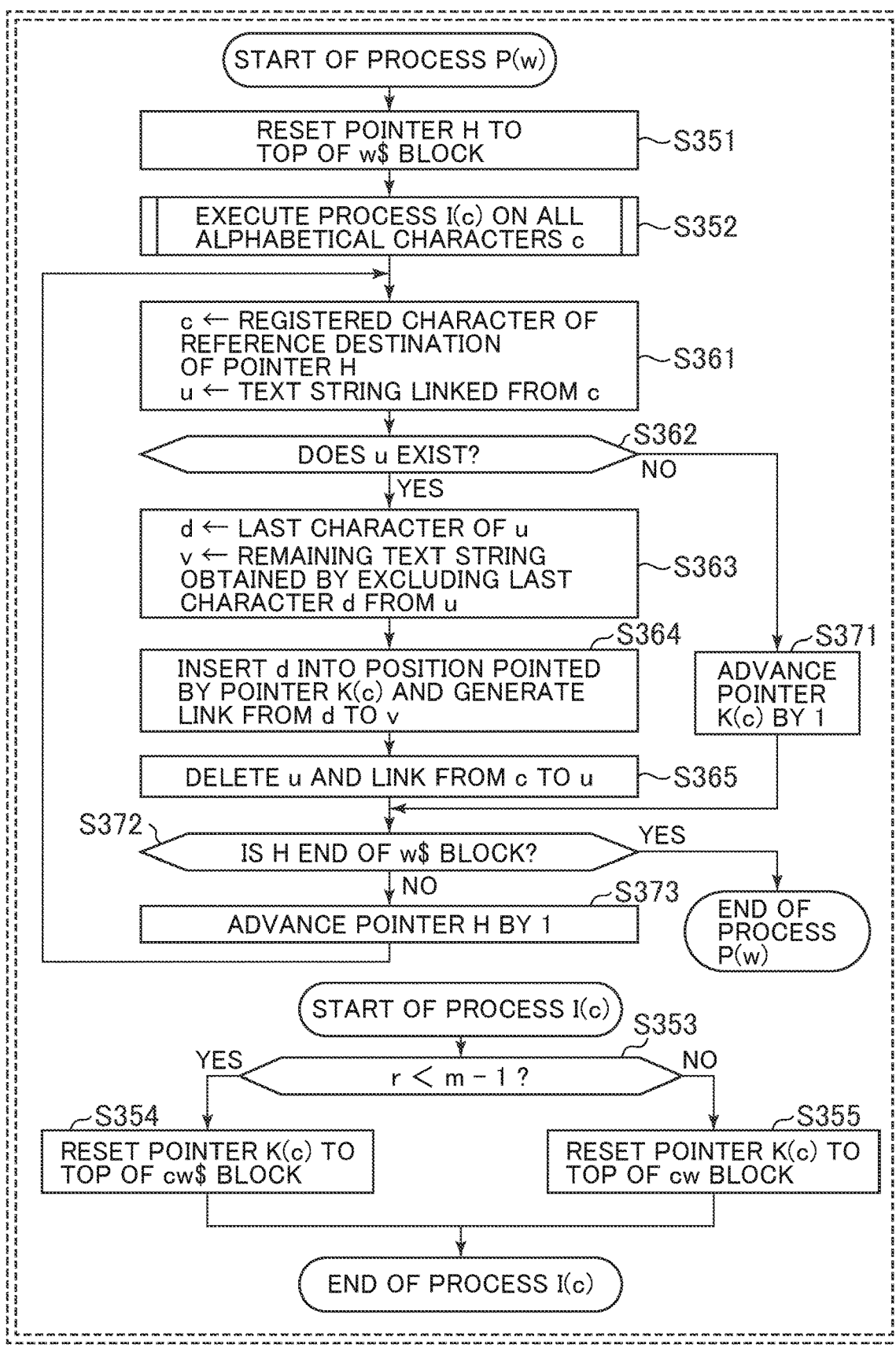
FIG. 5 is a flowchart showing details of a process P(w) and a process I(c) according to the embodiment of the present invention.

In S312, the multicore CPU 101 executes a process P(w) shown in FIG. 5 on all alphabetical text strings w each having a length of m in parallel.

In S313, the multicore CPU 101 increments the value m by 1.

In S314, the multicore CPU 101 determines whether or not m<r. If it is determined to be Yes in S314, the process returns to S312. If it is determined to be No in S314, the process proceeds to S321.

In S321, the multicore CPU 101 determines whether or not an unregistered text string linked from an entry within a block still remains. If it is determined to be Yes in S321, the process proceeds to S322. If it is determined to be No in S321, the process proceeds to S331.

Figure 6:
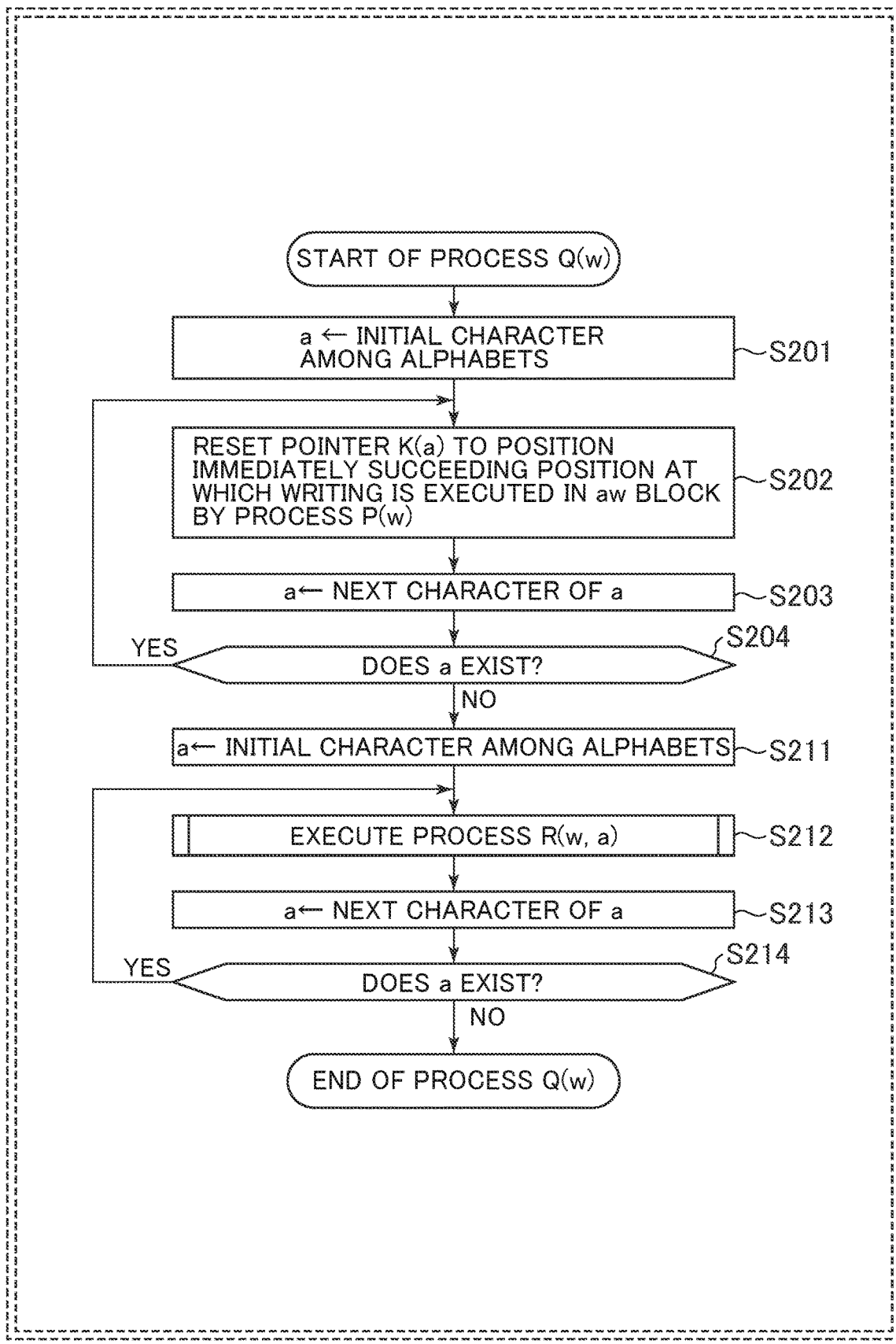
FIG. 6 is a flowchart showing details of a process Q(w) according to the embodiment of the present invention.

In S322, the multicore CPU 101 executes a process Q(w) shown in FIG. 6 on all alphabetical text strings w each having a length of r−1 in parallel.

In S331, the multicore CPU 101 generates coupled text strings for blocks by coupling entry characters registered in the blocks.

In S332, the multicore CPU 101 generates a single output text string obtained by coupling the coupled text strings obtained in S331 in the order of the labels of the blocks and outputs the output text string as the text string dictionary 112 to the HDD 103.

FIG. 5 is a flowchart showing details of the process P(w) called from S312 and a process I(c).

First, the process P(w) is described below.

In S351, the multicore CPU 101 resets a pointer H to the top of a w$ block.

In S352, the multicore CPU 101 executes the process I(c) on all alphabetical characters c.

In S361, the multicore CPU 101 sets a registered character of a reference destination of the pointer H to c and sets, to u, a text string (unregistered text string) linked from the registered character c.

In S362, the multicore CPU 101 determines whether or not the text string u set in S361 exists. If it is determined to be Yes in S362, the process proceeds to S363. If it is determined to be No in S362, the process proceeds to S371.

In S363, the multicore CPU 101 sets the last character of u to d and sets, to v, a remaining text string obtained by excluding the last character d from u.

In S364, the multicore CPU 101 inserts d into a position pointed by a pointer K(c) and generates a link from the inserted d to v.

In S365, the multicore CPU 101 deletes u and a link from c to u.

In S371, the multicore CPU 101 advances the pointer K(c) by 1 to the next entry.

In S372, the multicore CPU 101 determines whether or not H is at the end of the w$ block. If it is determined to be Yes in S372, the process P(w) is terminated. If it is determined to be No in S372, the process P(w) proceeds to S373.

In S373, the multicore 101 advances the pointer H by 1 to the next entry.

Next, the process I(c) is described below.

In S353, the multicore CPU 101 determines whether or not r<m−1. If it is determined to be Yes in S353, the process proceeds to S354. If it is determined to be No in S353, the process proceeds to step S355.

In S354, the multicore CPU 101 resets the pointer K(c) to the top of a cw$ block.

In S355, the multicore CPU 101 resets the pointer K(c) to the top of a cw block.

FIG. 6 is a flowchart showing details of the process Q(w) called from S322.

In S201, the multicore CPU 101 substitutes an initial character of alphabets into a variable a. For example, when alphabetical characters are of two types of A and T, an "A" is substituted into the variable a.

In S202, the multicore CPU 101 resets a pointer K(a) to a position immediately after a position at which writing to an aw block has been executed by the process P(w).

In S203, the multicore CPU 101 updates a to the next character of the alphabets. For example, when the alphabetical characters are of the two types of A and T, and the "A" is already substituted in the variable a, the next "T" is substituted into the variable a.

In S204, the multicore CPU 101 determines whether or not a can be substituted in S203 exists. If it is determined to be Yes in S204, the process returns to S202. If it is determined to be No in S204, the process proceeds to S211.

In S211, the multicore CPU 101 sets a to the initial character of the alphabets again in the same manner as S201.

Figure 7:
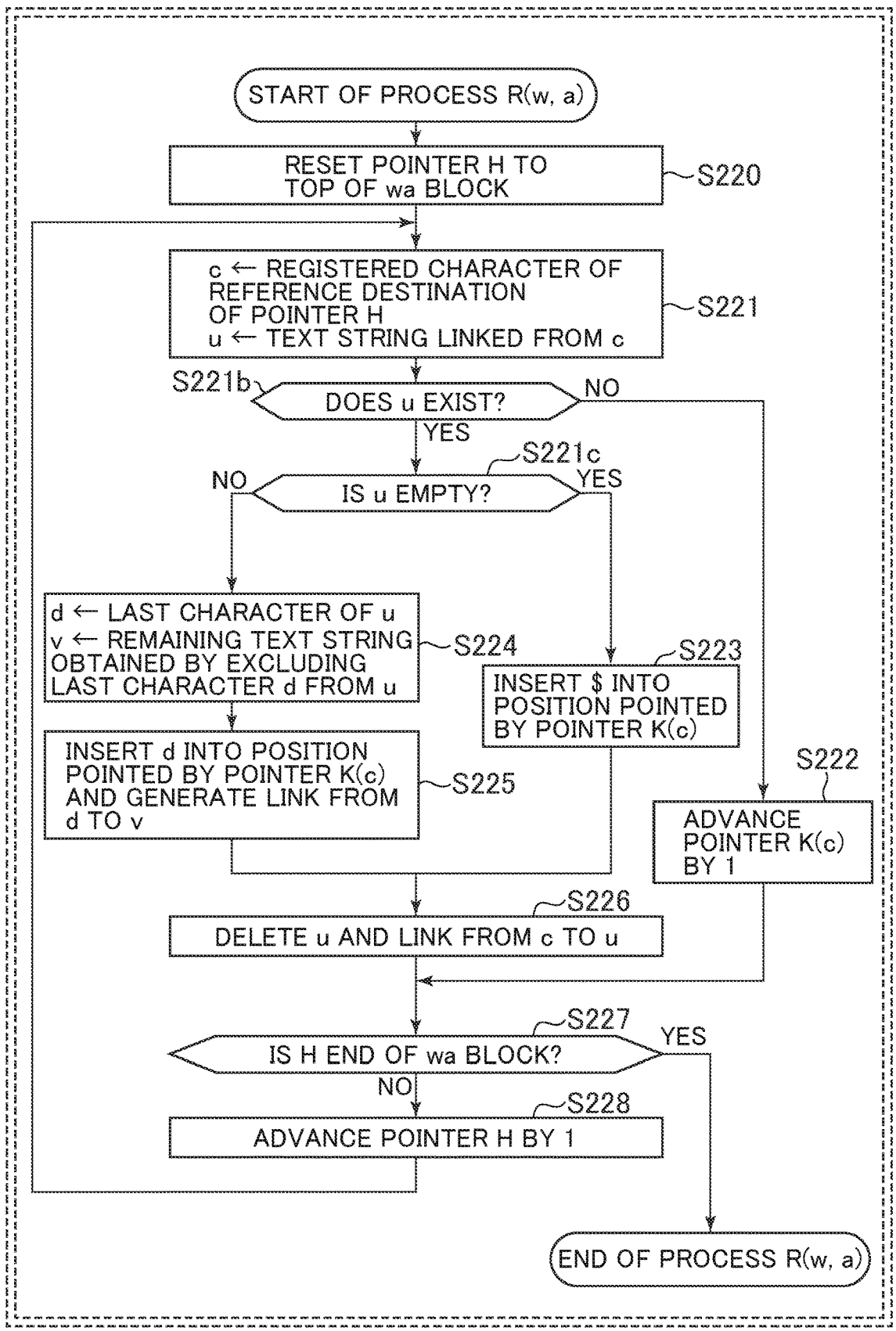
FIG. 7 is a flowchart showing details of a process R(w, a) according to the embodiment of the present invention.

In S212, the multicore CPU 101 sequentially executes a process R(W, a) shown in FIG. 7.

In S213, the multicore CPU 101 updates a to the next character of the alphabets in the same manner as S203.

In S214, the multicore CPU 101 determines whether or not a which can be substituted in S213 exists in the same manner as S204. If it is determined to be Yes in S214, the process returns to S212. If it is determined to be No in S214, the process Q(w) is terminated.

FIG. 7 is a flowchart showing details of the process R(w, a) called from S212.

In S220, the multicore CPU 101 resets the pointer H to the top of a wa block.

In S221, the multicore CPU 101 sets a registered character of a reference destination of the pointer H to c and sets, to u, a destination text string linked from c.

In S221*b*, the multicore CPU 101 determines whether or not u exists. If it is determined to be Yes in S221*b*, the process proceeds to S221*c*. If it is determined to be No in S221*b*, the process proceeds to S222.

In S221*c*, the multicore CPU 101 determines whether or not u is an empty text string E. If it is determined to be Yes in S221*c*, the process proceeds to S223. If it is determined to be No in S221*c*, the process proceeds to S224.

In S222, the multicore CPU 101 advances the point K(c) by 1 to the next entry.

In S223, the multicore CPU 101 inserts a delimiter $ into a position pointed by the pointer K(c).

In S224, the multicore CPU 101 sets the last character of u to d and sets, to v, a remaining text string obtained by excluding the last character d from u.

In S225, the multicore CPU 101 inserts d into a position pointed by the pointer K(c) and generates a link from d to v.

In S226, the multicore CPU 101 deletes u and a link from c to u.

In S227, the multicore CPU 101 determines whether or not H is the end of the wa block. If it is determined to be Yes in S227, the process R(w, a) is terminated. If it is determined to be No in S227, the process proceeds to S228.

In S228, the multicore CPU 101 advances the pointer H by 1 to the next entry.

The processes described using the flowcharts of FIGS. 3 to 7 are clarified by a specific example shown in FIGS. 8 to 12. The specific example describes a case where alphabetical characters forming the text string data 111 are of the two types of A and T and r=2.

In S301 (process of generating empty blocks), empty blocks are generated as a $ block, an A$ block, a T$ block, an AA block, an AT block, a TA block, and a TT block.

Figure 8:
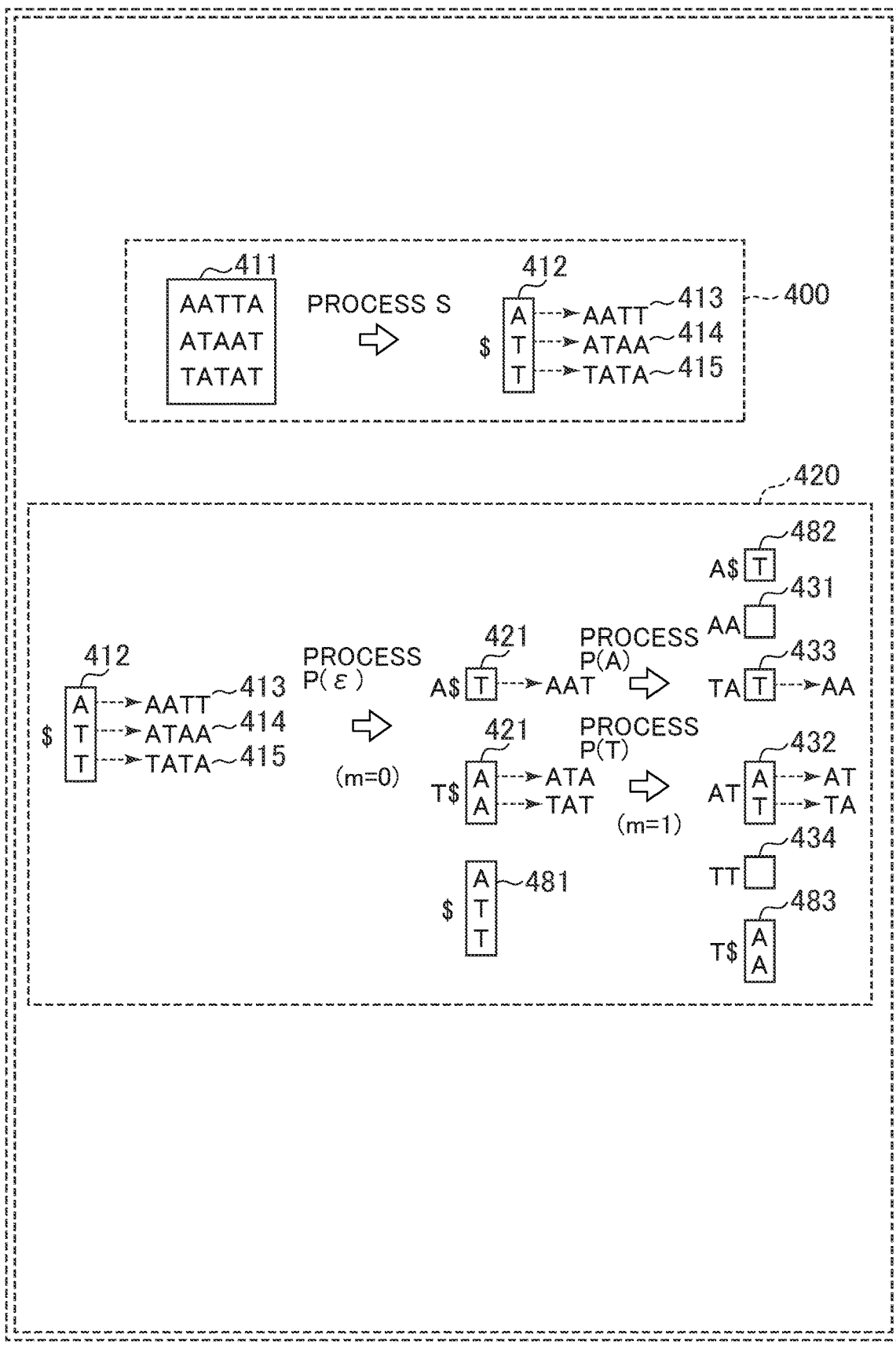
FIG. 8 is an explanatory diagram showing a specific example of a process S and the process P(w) according to the embodiment of the present invention.

FIG. 8 is an explanatory diagram showing a specific example of a process S and the process P(w).

In S302 (process S), the process indicated in a frame 400 is executed. Specifically, in the process S, the following 3 entries are registered in the $ block 412 that has been an empty block. Text string data 111 of 3 rows is read into a frame 411.

As the process S, a first row "AATTA" in the frame 411 is registered as a new A of the $ block 412 and an AATT (indicated by a symbol 413) that is a destination of a link from the new A.

As the process S, a second row "ATAAT" in the frame 411 is registered as a new T of the $ block 412 and an ATAA (indicated by a symbol 414) that is a destination of a link from the new T.

As the process S, a third row "TATAT" in the frame 411 is registered as a new T of the $ block 412 and a TATA (indicated by a symbol 415) that is a destination of a link from the new T.

As indicated in a frame 420, in the first (m=0) process P(w) called from S312, the characters are registered in different blocks from the 3 entries of the $ block 412, respectively. A text string w having a length of m=0 is only an empty text string E. Thus, when m=0, only a process P(E) is executed.

As the process P(E), the AATT (indicated by the symbol 413) linked from the A of the $ block 412 is registered as a new T of an A$ block 421 and an AAT that is a destination of a link from the new T. After the registration, the A of the $ block 412, the AATT (indicated by the symbol 413) which is the destination of the link from the A, and the link are deleted.

As the process P(E), the ATAA (indicated by the symbol 414) linked from the T of the $ block 412 is registered as a new A of a T$ block 422 and an ATA that is a destination of a link from the new A. After the registration, the T of the $ block 412 is kept as it is, and the ATAA (indicated by the symbol 414) which is the destination of the link from the T, and the link are deleted.

As the process P(E), the TATA (indicated by the symbol 415) linked from the T of the $ block 412 is registered as a new A of the T$ block 422 and a TAT that is a destination of a link from the new A. After the registration, the T of the $ block 412 is kept as it is, and the TATA (indicated by the symbol 415) which is the destination of the link from the T, and the link are deleted. Thus, the $ block 412 becomes a $ block 481.

The following example is described with reference to the process P(w) shown in FIG. 5. In the example, the AATT (indicated by the symbol 413) linked from the A of the $ block 412 is registered as the new T of the A$ block 421 and the AAT that is the destination of the link from the T, and, after the registration, the A of the $ block 412 is kept as it is, and the AATT (indicated by the symbol 413) which is the destination of the link from the A, and the link are deleted.

An unregistered text string to be registered in the aforementioned example is the "AATT (indicated by the symbol 413)". A registration source block to which an entry that is a source of the link to the unregistered text string belongs is the "$ block 412".

The flowchart is described above assuming a case where, in the process P(w), the registration source block is the w$ block (S351), the unregistered text string is the text string u (S361), and the entry that is the source of the link is the character c at a position pointed by the pointer H (S361).

A registration destination block in which the unregistered text string is to be registered in the aforementioned example is the "A$ block 421". The entry "T" newly registered in the registration destination block is the last character of the unregistered text string "AATT". The text string "AAT" that is the destination of the link from the entry "T" is remaining characters obtained by excluding the last character of the unregistered text string "AATT" therefrom.

The flowchart is described above in a case where, in the process P(w), the registration destination block is the cw$ block (S354) or the cw block (S355), the newly registered entry is the character d (S363) inserted into a position pointed by the pointer K(c), and the newly registered text string of the link destination is the text string v (S363).

As indicated in the frame 420, in the second (m=1) process P(w) called from S312, a process P(A) and a process P(T) are executed in parallel, since the text string w having the length of m are of the two types of A and T. In other words, a set of blocks handled in the process P(A) and a set of blocks handled in the process P(T) are categorized into two groups as respective partial processes which are executable independently of each other.

As the process P(A), the AAT linked from the T of the A$ block 421 is registered as a new T of a TA block 433 and an AA that is a destination of a link from the T. After the registration, the T of the A$ block 421 is kept as it is, and the AAT which is the destination of the link from the T, and the link are deleted. Thus, the A$ block 421 becomes an A$ block 482 in which only an entry T remains. In addition, an AA block 431 is not a registration destination block as the process P(A) executed at this time, but is used in the next process (indicated in a frame 435). Thus, the AA block 431 is herein described for easy understanding. Blocks that are not registration destination blocks are therefore shown in the drawings where appropriate.

As the process P(T), the ATA linked from the A of the T$ block 422 is registered as a new A of an AT block 432 and an AT that is a destination of a link from the A. After the registration, the A of the T$ block 422 is kept as it is, and the ATA which is the destination of the link from the A, and the link are deleted.

As the process P(T), the TAT linked from the A of the T$ block 422 is registered as a new T of the AT block 432 and a TA that is a destination of a link from the T. After the registration, the A of the T$ block 422 is kept as it is, and the TAT which is the destination of the link from the A, and the link are deleted.

After that, since m=r=2 and it is determined to be No in S314, the third (m=2) process P(w) is not executed.

Since the unregistered text string "AA" of the TA block 433 or the like still remains, S it is determined to be Yes in 321 and S322 is executed.

Figure 9:
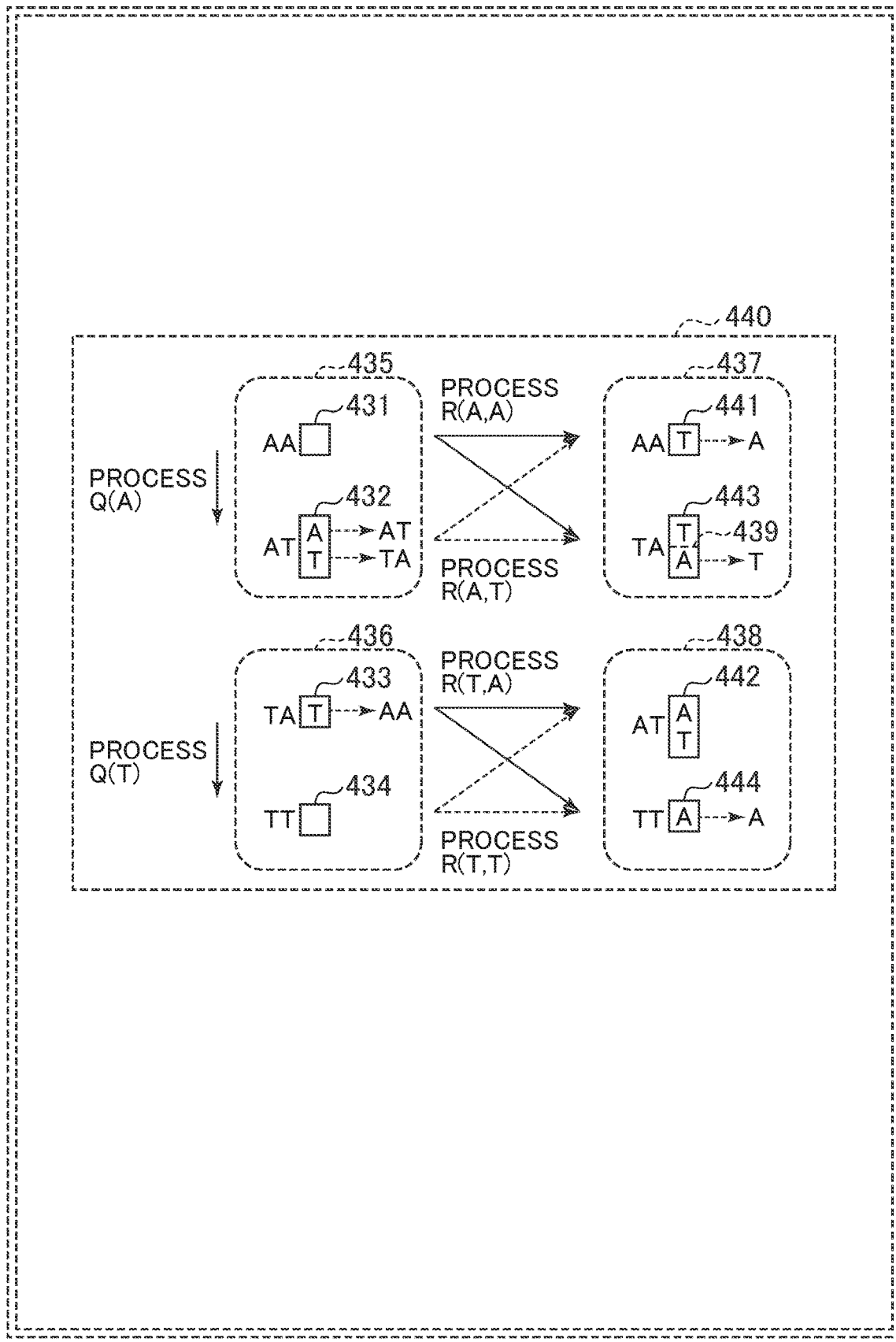
FIG. 9 is an explanatory diagram showing a specific example of the process Q(w) and the process R(w, a) that are executed after the processes in FIG. 8 according to the embodiment of the present invention.

FIG. 9 is an explanatory diagram showing a specific example of the process Q(w) and the process R(w, a) that are executed after the process in FIG. 8.

As indicated in a frame 440, in the first process Q(w) called from S322, all alphabetical text strings having a length of r−1 are of the two types of A and T, and a process Q(A) and a process Q(T) are executed in parallel.

In S212 included in the process Q (A), a process R (A, A) and a process R(A, T) are sequentially executed in this order on characters a=A, T.

An input group (indicated in the frame 435) of the process Q(A) and an output group (indicated in a frame 437) of the process Q(A) are shown.

Blocks to be sequentially referenced are collected and grouped into the input group of the process Q(A). Blocks to be simultaneously written in parallel are collected and grouped into the output group of the process Q(A).

As the process R(A, A) of the process Q(A), the process is skipped, since an entry having a link does not exist in the AA block 431.

As the process R(A, T) of the process Q(A), the AT linked from the A of the AT block 432 is registered as a new T of an AA block 441 and an A that is a destination of a link from the T. After the registration, the A of the AT block 432 is kept as it is, and the AT which is the destination of the link from the A, and the link are deleted.

As the process R(A, T) of the process Q(A), the TA linked from the T of the AT block 432 is registered as a new A of a TA block 443 and a T that is a destination of a link from the A. After the registration, the T of the AT block 432 is kept as it is, and the TA which is the destination of the link from the T, and the link are deleted.

The following example is described with reference to R(w, a) shown in FIG. 7. In the example, the AT linked from the A of the AT block 432 is registered as the new T of the AA block 441 and the A that is the destination of the link from the new T, the A of the AT block 432 remains after the registration, and the AT, which is the destination of the link from the A, and the link are deleted.

An unregistered text string to be registered in the aforementioned example is the "AT". A registration source block to which an entry that is a source of a link to the unregistered text string belongs is the "AT block 432".

The flowchart is described above assuming a case where, in R(w, a), the registration source block is the wa block (S220), the unregistered text string is the text string u (S221), and the entry that is the source of the link is the character c at a position pointed by the pointer H (S221).

A registration destination block in which the unregistered text string is to be registered in the aforementioned example is the "AA block 441". The entry "T" newly registered in the registration destination block is the last character of the unregistered text string "AT". The text string "A" that is the destination of the link from the entry "T" is a character obtained by excluding the last character of the unregistered text string "AT" therefrom.

The flowchart is described above assuming a case where, in R(w, a), the registration destination block is the aw block (S202), the newly registered entry is the character d inserted into the position pointed by the pointer K(c) (S224), and the newly registered text string that is the destination of the link is the text string v (S224). That is, a registration destination block in R(w, a) is a group of cw blocks (c is a freely selected character) and is common to all a's and takes over and uses the same pointer K(c) reset in S202. As a result, writing to the cw blocks is appropriately executed in the order of the dictionary.

In S212 included in the process Q(T), a process R(T, A) and a process R(T, T) are sequentially executed in this order on the characters a=A, T.

An input group (indicated in a frame 436) of the process Q(T) and an output group (indicated in a frame 438) of the process Q(T) are shown.

As the process Q(T) and the process R(T, A), the AA linked from the T of the TA block 433 is registered as a new A of a TT block 444 and an A that is a destination of a link from the A. After the registration, the T of the TA block 433 is kept as it is, and the AA which is the destination of the link from the T, and the link are deleted.

As the process R(T, T) of the process Q(T), the process is skipped, since an entry having a link does not exist in the TT block 434.

Since the unregistered text string "A" of the AA block 441 and the like still remain, it is determined to be Yes in S321 and S322 is executed.

Figure 10:
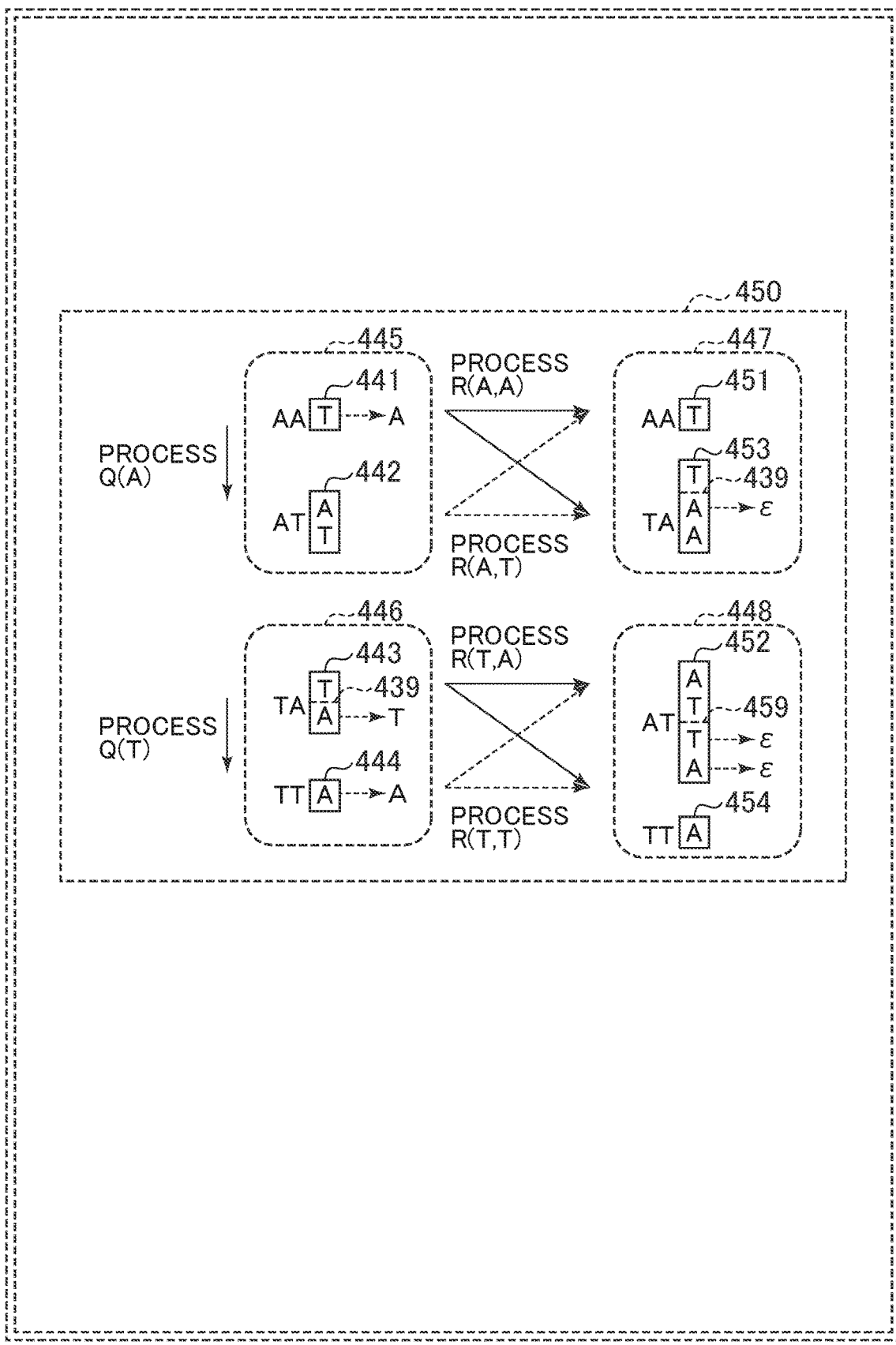
FIG. 10 is an explanatory diagram showing a specific example of the process Q(w) and the process R(w, a) that are executed after the processes in FIG. 9 according to the embodiment of the present invention.

FIG. 10 is an explanatory diagram showing a specific example of the process Q(w) and the process R(w, a) that are executed after the processes in FIG. 9.

As indicated in a frame 450, the process Q(A) and the process Q(T) are executed in parallel also in the second process Q(w).

An input group (indicated in a frame 445) of the process Q(A) and an output group (indicated in a frame 447) of the process Q(A) are shown.

As the process R(A, A) of the process Q(A), the A linked from the T of the AA block 441 is registered as a new A of a TA block 453 and an E that is a destination of a link from the A. An insertion position 439 for this registration is pointed by a pointer K(T). After the registration, the T of the AA block 441 remains after the registration, the A which is the destination of the link from the T, and the link are deleted.

As the process R(A, T) of the process Q(T), the process is skipped, since an entry having a link does not exist in the AT block 442. Specifically, a pointer K(A) to the inside of an AA block 451 and a pointer K(T) to the inside of the TA block 453 are advanced.

An input group (indicated in a frame 446) of the process Q(T) and an output group (indicated in a frame 448) of the process Q(T) are shown.

As the process R(T, A) of the process Q(T), the T linked from the A of the TT block 443 is registered as a new T of an AT block 452 and an E that is a destination of a link from the T. An insertion position 459 for this registration is pointed by the pointer K(A). After the registration, the A of the TT block 443 is kept as it is, the T which is the destination of the link from the A, and the link are deleted.

As the process R(T, T) of the process Q(T), the A linked from the A of the TT block 444 is registered as a new A of the AT block 452 and an ε that is a destination of a link from the A. After the registration, the A of the TT block 444 is kept as it is, and the A which is the destination of the link from the A, and the link are deleted.

Since the unregistered text string "E" of the TA block 453 or the like still remains, it is determined to be Yes in S321 and S322 is executed.

Figure 11:
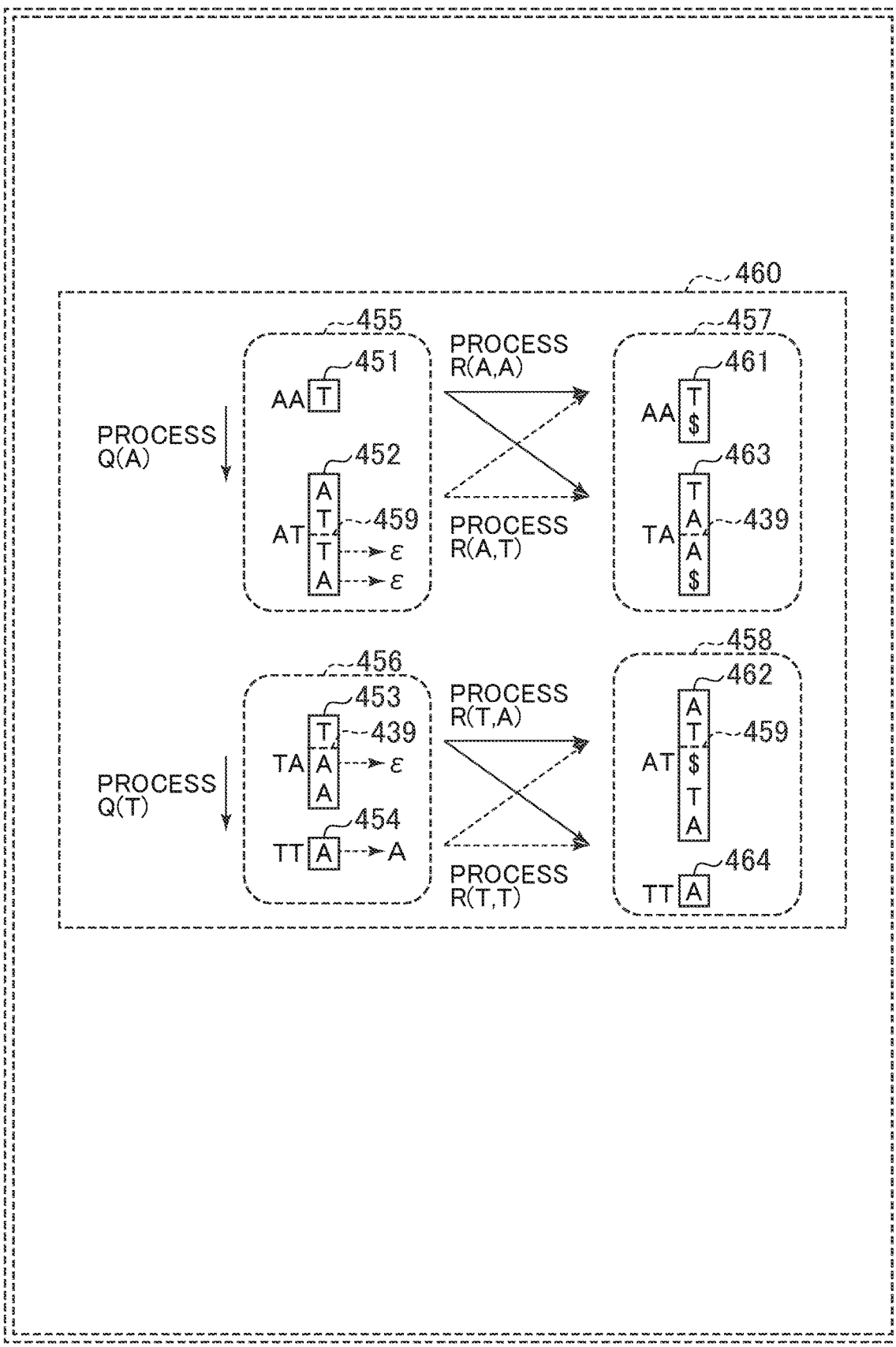
FIG. 11 is an explanatory diagram showing a specific example of the process Q(w) and the process R(w, a) that are executed after the processes in FIG. 10 according to the embodiment of the present invention.

FIG. 11 is an explanatory diagram showing a specific example of the process Q(w) and the process R(w, a) that are executed after the processes in FIG. 10.

As indicated in a frame 460, the process Q(A) and the process Q(T) are executed in parallel also in the third process Q(w).

An input group (indicated in a frame 455) of the process Q(A) and an output group (indicated in a frame 457) of the process Q(A) are shown.

As the process R (A, A) of the process Q (A), the process is skipped, since an entry having a link does not exist in the AA block 451. Specifically, the pointer K(A) to the inside of an AA block 461 and the pointer K(T) to the inside of a TA block 463 are advanced.

As the process R(A, T) of the process Q(A), the E linked from a T of the AT block 452 is registered as a new $ of the TA block 463. After the registration, the T of the AT block 452 is kept as it is, and the ε which is the destination of the link from the T, and the link are deleted.

As the process R(A, T) of the process Q (A), the ε linked from the A of the AT block 452 is registered as a new $ of the AA block 461. After the registration, the A of the AT block 452 is kept as it is, the ε which is the destination of the link from the A, and the link are deleted.

An input group (indicated in a frame 456) of the process Q(T) and an output group (indicated in a frame 458) of the process Q(T) are shown.

As the process R(T, A) of the process Q(T), the ε linked from the A of the TA block 453 is registered as a new $ of an AT block 462. While the A of the TA block 453 remains after the registration, the ε which is the destination of the link from the A, and the link are deleted.

As the process R(T, T) of the process Q(T), the process is skipped, since an entry having a link does not exist in the TT block 454. Specifically, the pointer K (A) to the inside of the AT block 462 and the pointer K(T) to the inside of a TT block 464 are advanced.

Since all the unregistered text strings have been processed by this, it is determined to be No in S321 and S331 is executed.

Figure 12:
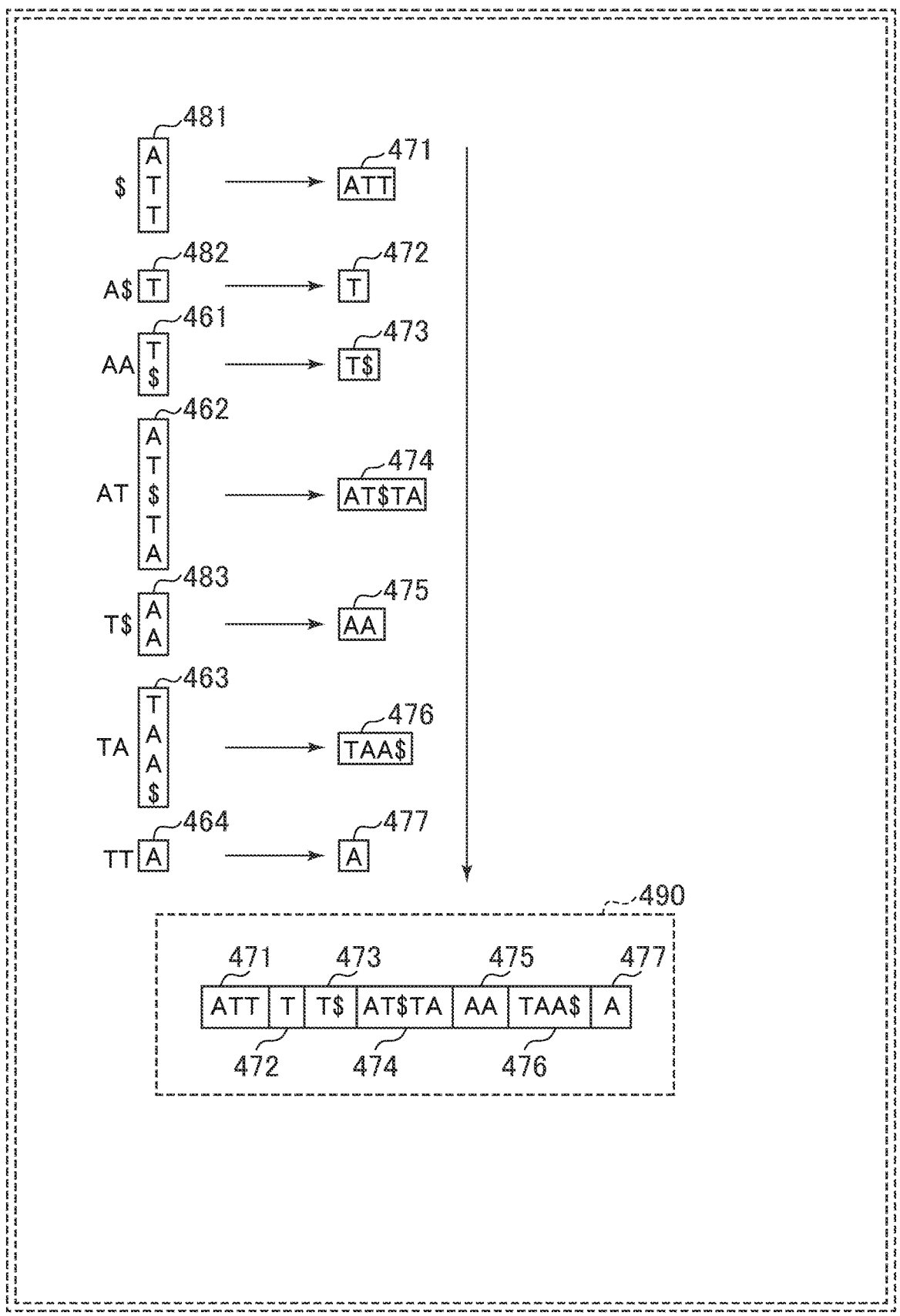
FIG. 12 is an explanatory diagram showing a process of outputting a text string dictionary after the processes in FIG. 11 according to the embodiment of the present invention.

FIG. 12 is an explanatory diagram showing a process of outputting the text string dictionary 112 after the processes in FIG. 11.

In S331 (a step of generating coupled text strings for each block), entries registered in blocks ($ block 481, A$ block 482, AA block 461, AT block 462, T$ block 483, TA block 463, and TT block 464) sorted in the order of the labels are extracted as text strings 471 to 477 in the order of arrows shown in the drawing.

In S332 (a step of outputting the text string dictionary 112), a single coupled output text string is generated as the text string dictionary 112 by coupling the text strings 471 to 477 in this order, as indicated in a frame 490.

In the aforementioned embodiment, as the step of generating the text string dictionary 112 (S231), the text string data analyzing device 1 receives text strings from the text string data 111 via the NIF 104. The text string data analyzing device 1 takes the received text strings as unregistered text strings and sequentially registers all suffixes of the text strings in empty blocks in order from the shortest suffix in accordance with the procedures for the process P(w), the process Q(w), and the process R(w, a).

Registering the suffixes in the blocks indicates that characters preceding the suffixes (however, delimiters $ when the suffixes match the entire text strings) are registered in the blocks. An efficient calculation method for decoding the suffixes succeeding the characters registered in the blocks is known (Nonpatent Literature 1). In addition, a remaining text string obtained by excluding the suffix from the unregistered text string is linked to the registered suffix and is temporarily held.

After the process of registering all the suffixes of all the text strings in the blocks is completed, a text string is generated by coupling characters registered in all the blocks in accordance with the procedure shown in FIG. 12, and the text string dictionary 112 obtained by coupling the text strings in lexicographic order of labels of the blocks is subjected to BW transform and output to the HDD 103.

In S301, when the already generated text string dictionary 112 exists in the HDD 103 (or is extracted via the NIF 104 from a connection destination of the network and stored in the HDD 103), information on blocks upon the generation of the text string dictionary 112 may be loaded in the memory, instead of empty blocks. In this case, text string data 111 newly received via the NIF 104 can be additionally registered in the already generated text string dictionary 112.

As described with S364, S223, and S225, in the case where a new entry is additionally registered in a block in the memory 102 each time, a process of inserting in the block, which is a list, is required. Thus, as a data structure of the block, a dynamic structure (like a balanced tree described in Nonpatent Literature 4) or a static structure (like a static structure obtained by regenerating a copy of a list each time as described in Patent Literature 1) may be used.

A supplementary description is given to explain a parallelization degree, waiting, and the like in parallel calculation in the process of generating the text string dictionary 112 according to the embodiment.

In the aforementioned example, alphabetical characters are of the two types of A and T. The number of types of alphabetical characters, however, is increased to h (or the alphabet characters are characters $a_1, a_2, \ldots, a_h$).

First, a parallelization degree of processes P(w) is described.

A registration source block from which read is executed in the process P(w) is the w$ block. When text strings w are different for respective m's, registration source blocks to be read are different from each other.

When m is smaller than r−1, registration destination blocks to which writing is executed in the process P(w) are an $a_1$w$ block, an $a_2$w$ block, . . . , and an $a_h$w$ block. When m=r−1, registration destination blocks to which writing is executed in the process P(w) are an $a_1$w block, an $a_2$w block, . . . , and an $a_h$w block. In both cases, when the text strings w are different, the registration destination blocks are mutually exclusive. Thus, the processes P(w) can be executed independently of each other in parallel without interfering with each other.

Next, a parallelization degree of processes Q(w) is described.

Registration source blocks from which reading is executed in the process Q(w) are a $wa_1$ block, a $wa_2$ block, . . . , and a $wa_n$ block. When text strings w are different, the registration source blocks are mutually exclusive.

Registration destination blocks to which writing is executed in the process Q(w) are an $a_1$w block, an $a_2$w block, and an $a_h$w block. When the text strings w are different, the registration source blocks are mutually exclusive. Thus, the processes Q(w) can be executed independently of each other in parallel without interfering with each other.

A parallelization degree of processes R(w, a) is described.

The number of registration destination blocks in a process R(w, $a_1$), a process R(w, $a_2$), and a process R(w, $a_h$) is h. The registration destination blocks are common to the $a_1$w block, the $a_2$w block, and the $a_h$w block. Since the registration processes are sequentially executed in alphabetical order, processes of registering in the blocks are appropriately executed in alphabetical order.

The number of processes R(w, a) to be sequentially executed in order is equal to an alphabet size and is constant without depending on the parameter r. Thus, even when the parameter r is increased and a degree of the division of the parallel process is increased, the length of a time period for waiting for the sequential execution is maintained at a constant value and a reduction in CPU utilization due to the waiting does not occur.

As described above, the process is divided into the partial processes executable independently of each other, waiting is not necessary in a time period other than a time period for sequentially executing the processes R(w, $a_1$), R(w, $a_2$), . . . , and R(w, $a_h$), and a reduction in processor utilization due to waiting can be avoided.

In this case, the multicore CPU 101 may receive the value of the positive integer parameter r or automatically calculate the value of the positive integer parameter r based on the number of CPU cores of the multicore CPU 101.

As described with S301, when r=2 and alphabetical characters are of the two types of A and T, blocks ($ block, A$ block, T$ block, AA block, AT block, TA block, and TT block) of seven types are used. Specifically, the number of blocks can be calculated according to an equation "(the number of blocks)=$((h^{(r+1)}-1)/(h-1))$" obtained by generalizing an equation "$7=2^3-1$". Then, the multicore CPU 101 can calculate the number of blocks based on the number of CPU cores so that (the number of CPU cores)×K=(the number of blocks) (K is, for example, a constant number in a range of 10 to 90 indicating several tens of times). Then, the multicore CPU 101 can substitute the calculated number of blocks into the equation obtained by the generalization, thereby automatically calculating the parameter r.

When the positive integer parameter r is increased, the number of blocks is exponentially increased. Thus, the value of r can be determined so that the number of blocks is several tens of times larger than the number of CPU cores. In this case, even when dynamic load distribution is executed by multithreading, and calculation time in the processes P(w) and Q(w) varies, calculation loads of the cores can be equalized and the speed can be efficiently increased by effectively using all the cores.

For example, the number of processes Q(w) executable independently of each other in parallel is equal to the number of text strings w having a length of r−1. When the alphabet size is h, the number of processes Q(w) executable independently of each other in parallel is equal to $h^{(r-1)}$. Thus, even when h=4 like the case of DNA sequence data, r can be selected so that the number of processes Q(w) is several tens of times larger than the number of usable CPU cores.

It is, therefore, possible to provide a method for dividing a process into partial processes of which number is several tens of times larger than the number of CPU cores and a method for avoiding a reduction, caused by waiting between partial processes, in processor utilization.

The present invention is not limited to the aforementioned examples and includes various modified examples. For example, the examples are described to clearly explain the present invention and are not necessarily limited to all the configurations described above.

In addition, a portion of a configuration described in a certain example can be replaced with a configuration described in another example. Furthermore, a configuration described in a certain example can be added to a configuration described in another example.

In addition, a configuration described in a certain example can be added to or replaced with a configuration described in another example, and a configuration described in a certain example can be removed. Furthermore, a portion or all of the aforementioned configurations, functions, processing units, processing means, and the like may be enabled by hardware that is, for example, designed with an integrated circuit.

In addition, the aforementioned configurations, the aforementioned functions, and the like may be enabled with software by causing a processor to interpret and execute a program for enabling the functions.

Information such as the program enabling the functions, tables, and files can be stored in a recording device such as a memory, a hard disk, or a solid state drive (SSD) or a recording medium such as an integrated circuit (IC) card, an SD card, or a digital versatile disc (DVD).

In addition, control lines and information lines that are considered to be necessary for the description are shown. All control lines and all information lines that are necessary for a product are not necessarily shown. Actually, it may be considered that almost all configurations are connected to each other.

LIST OF REFERENCE SIGNS

1 Text string data analyzing device
101 Multicore CPU
102 Memory
103 HDD
104 NIF
105 Input unit
106 Display/output unit
107 Bus
111 Text string data
112 Text string dictionary
121 Query string
122 Search results
501 Patients
502 DNA samples
503 DNA sequencer
504 DNA sequence data
505 DNA sequence dictionary
521 Analysis instruction
522 Analysis results
511 Genetic panel
512 Database

The invention claimed is:

1. A method for generating a text string dictionary,
    the method being executed by a text string data analyzing device including a multicore CPU having a plurality of CPU cores and a memory,
    the text string dictionary loaded in the memory being divided into a plurality of blocks, the blocks being added thereto respective labels different from each other, the label including an alphabet constituting text string data and one or more delimiters,
    the method for generating a text string dictionary comprising the steps, performed by the multicore CPU, of:
    registering, for each of the inputted text string data, the last character of the received text string data as an entry of the block in the blocks added thereto the labels of the delimiters, and making the last character associate with a remaining text string obtained by excluding the last character from the text string data, as an unregistered text string;
    executing an entry registration process in parallel on each of the blocks grouped into appropriate blocks executable independently of each other, the entry registration process comprising the substep of reading registration source blocks in which the unregistered text strings are associated with the entries of the blocks, the substep of registering last characters of the unregistered text strings of the registration source blocks as new entries in registration destination blocks identified from the labels and entries of the registration source blocks, and the substep of associating remaining text strings obtained by excluding the new entries from the unregistered text strings as new unregistered text strings; and
    outputting, as Burrows-Wheeler (BW) transformed data of the text string dictionary in which the text string data is already registered, a text string obtained by coupling text strings registered in the entries of the blocks in the order of alphabets indicated by the labels of the blocks and the delimiters in a state in which no unregistered text strings of the blocks exists.

2. The method for generating a text string dictionary according to claim 1,
    further comprising the step, performed by the multicore CPU, of calculating, based on the number of cores included in the multicore CPU, lengths of the labels of the blocks that are used to determine the number of blocks to be loaded into the memory.

3. The method for generating a text string dictionary according to claim 1,
    further comprising the substeps in the entry registration process, performed by the multicore CPU, of: grouping the registration source blocks to be sequentially read and the registration destination blocks to be simultaneously written; executing, in parallel, processes of reading the registration source blocks between the groups of the registration source blocks; and sequentially executing processes of reading the registration source blocks in each of the groups of the registration source blocks.

4. A method for searching a text string dictionary, the method executed by a searching device including a storage means configured to store the text string dictionary generated by the method for generating a text string dictionary according to claim 1, and a control means, the method for searching a text string dictionary comprising the steps, performed by the control means, of:
receiving an input query string via an input means;
searching the number of appearances of the query string in the text string data registered in the text string dictionary; and
outputting the searched number of appearances via an output means.

5. The method for searching a text string dictionary according to claim 4,
wherein the text string dictionary is a DNA sequence dictionary in which DNA sequence data that is results of causing a DNA sequencer to analyze each of DNA samples of respective patients is registered as the text string data,
the method for searching a text string dictionary further comprising:
the step, performed by the input means, of receiving, as the query string, mutant DNA sequence data preset as a genetic panel;
the step, performed by the control means, of searching the number of appearances of the query string in the text string data registered in the text string dictionary, thereby analyzing whether or not mutation exists in the DNA sequence data of the patients, and
the step, also performed by the control means, of outputting appearing mutant DNA sequence data and supplementary information associated with the DNA sequence data in the genetic panel via the output means.

6. A system for processing a text string dictionary, comprising:
the text string data analyzing device configured to execute the method for generating a text string dictionary according to claim 1;
a searching device configured to execute a method for searching a text string dictionary, the method executed by a searching device including a storage means configured to store the text string dictionary generated by the method for generating a text string dictionary, and a control means, the method for searching a text string dictionary comprising the steps, performed by the control means, of:
receiving an input query string via an input means;
searching the number of appearances of the query string in the text string data registered in the text string dictionary; and
outputting the searched number of appearances via an output means,
wherein the text string dictionary is a DNA sequence dictionary in which DNA sequence data that is results of causing a DNA sequencer to analyze each of DNA samples of respective patients is registered as the text string data,
the method for searching a text string dictionary further comprising:
the step, performed by the input means, of receiving, as the query string, mutant DNA sequence data preset as a genetic panel;
the step, performed by the control means, of searching the number of appearances of the query string in the text string data registered in the text string dictionary, thereby analyzing whether or not mutation exists in the DNA sequence data of the patients, and
the step, also performed by the control means, of outputting appearing mutant DNA sequence data and supplementary information associated with the DNA sequence data in the genetic panel via the output means; and
the DNA sequencer configured to analyze DNA samples of patients and output results of the analysis as DNA sequence data in the method for searching a text string dictionary.

* * * * *